United States Patent [19]

Rizoiu et al.

[11] Patent Number: 5,741,247
[45] Date of Patent: Apr. 21, 1998

[54] ATOMIZED FLUID PARTICLES FOR ELECTROMAGNETICALLY INDUCED CUTTING

[75] Inventors: Ioana M. Rizoiu, Capistrano Beach; Andrew I. Kimmel, San Clemente, both of Calif.

[73] Assignee: Biolase Technology, Inc., San Clemente, Calif.

[21] Appl. No.: 522,503

[22] Filed: Aug. 31, 1995

[51] Int. Cl.$^6$ ............................................. A61N 5/02
[52] U.S. Cl. ........................... 606/10; 606/2; 606/3; 606/15
[58] Field of Search ........................ 83/22, 53, 168, 83/169, 177; 125/1, 2, 9–11.01, 11.07, 25–27, 30.01; 299/3, 10, 16, 17, 69, 95; 219/121.6, 121.67, 121.68, 121.7, 121.73–121.75, 121.84; 606/2–19; 128/897; 604/20

[56] References Cited

U.S. PATENT DOCUMENTS

| | | |
|---|---|---|
| 4,826,431 | 5/1989 | Fujimura et al. . |
| 5,151,029 | 9/1992 | Levy . |
| 5,199,870 | 4/1993 | Steiner et al. . |
| 5,267,856 | 12/1993 | Wolbarsht et al. . |
| 5,318,562 | 6/1994 | Levy et al. . |
| 5,388,988 | 2/1995 | Goisser et al. . |
| 5,401,171 | 3/1995 | Paghdiwala . |
| 5,409,376 | 4/1995 | Murphy . |

*Primary Examiner*—David M. Shay
*Attorney, Agent, or Firm*—Kenton R. Mullins

[57] ABSTRACT

An electromagnetically induced cutting mechanism which can provide accurate cutting operations on both hard and soft materials is disclosed. The electromagnetically induced cutter is capable of providing extremely fine and smooth incisions, irrespective of the cutting surface. Additionally, a user programmable combination of atomized particles allows for user control of various cutting parameters. The various cutting parameters may also be controlled by changing spray nozzles and electromagnetic energy source parameters. Applications for the cutting mechanism include medical, dental, industrial (etching, engraving, cutting and cleaning) and any other environments where an objective is to precisely remove surface materials without inducing thermal damage, uncontrolled cutting parameters, and/or rough surfaces inappropriate for ideal bonding. The cutting mechanism further does not require any films of water or any particularly porous surfaces to obtain very accurate and controllable cutting.

13 Claims, 5 Drawing Sheets

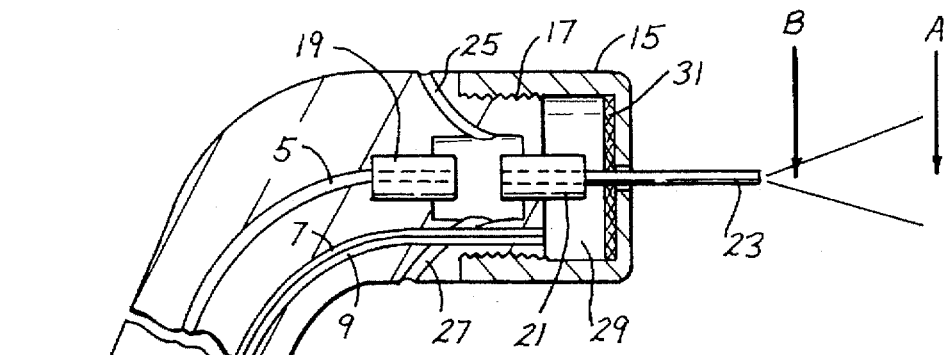
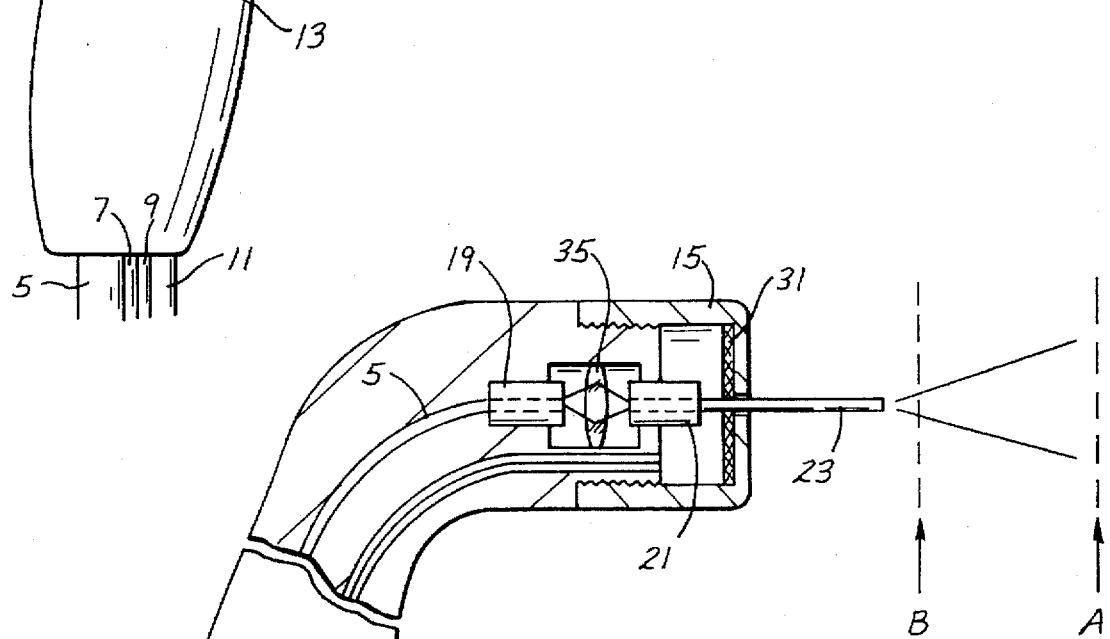
Fig. 1
PRIOR ART
Fig. 2

ATOMIZED FLUID PARTICLES FOR ELECTROMAGNETICALLY INDUCED CUTTING

BACKGROUND OF THE INVENTION

The present invention relates generally to a device for cutting both hard and soft materials and, more particularly, to a device for combining electromagnetic and hydro energies for cutting and removing both hard and soft tissues.

Turning to FIG. 1, a prior art optical cutter for dental use is disclosed. According to this prior art apparatus, a fiber guide tube 5, a water line 7, an air line 9, and an air knife line 11 (which supplies pressurized air) are fed into the hand-held apparatus 13. A cap 15 fits onto the hand-held apparatus 13 and is secured via threads 17. The fiber guide tube 5 abuts within a cylindrical metal piece 19. Another cylindrical metal piece 21 is a part of the cap 15.

When the cap 15 is threaded onto the hand-held device 13, the two cylindrical metal tubes 19 and 21 are moved into very close proximity of one another. A gap of air, however, remains between these two cylindrical metal tubes 19 and 21. Thus, the laser within the fiber guide tube 5 must jump this air gap before it can travel and exit through another fiber guide tube 23. Heat is dissipated as the laser jumps this air gap.

The pressurized air from the air knife line 11 surrounds and cools the laser as the laser bridges the gap between the two metal cylindrical objects 19 and 21. Thus, a first problem in this prior art apparatus is that the interface between the two metal cylindrical objects 19 and 21 has a dissipation of heat which must be cooled by pressurized air from the air knife line 11. (Air from the air knife line 11 flows out of the two exhausts 25 and 27 after cooling the interface between elements 19 and 21.) This inefficient interface between elements 19 and 21 results from the removability of the cap 15, since a perfect interface between elements 19 and 21 is not achieved.

The laser energy exits from the fiber guide tube 23 and is applied to a target surface within the patient's mouth, according to a predetermined surgical plan. Water from the water line 7 and pressurized air from the air line 9 are forced into the mixing chamber 29. The air and water mixture is very turbulent in the mixing chamber 29, and exits this chamber through a mesh screen with small holes 31. The air and water mixture travels along the outside of the fiber guide tube 23, and then leaves the tube and contacts the area of surgery. This air and water spray coming from the tip of the fiber guide tube 23 helps to cool the target surface being cut and to remove cut materials by the laser. The need for cooling the patient surgical area being cut is another problem with the prior art.

In addition to prior art systems which utilize laser light from a fiber guide tube 23, for example, to cut tissue and use water to cool this cut tissue, other prior art systems have been proposed. U.S. Pat. No. 5,199,870 to Steiner et al., which issued on Apr. 6, 1993, discloses an optical cutting system which utilizes the expansion of water to destroy and remove tooth material. This prior art approach requires a film of liquid having a thickness of between 10 and 200 mm. Another prior art system is disclosed in U.S. Pat. No. 5,267,856 to Wolbarsht et al., which issued on Dec. 7, 1993. This cutting apparatus is similar to the Steiner et al. patent, since it relies on the absorption of laser radiation into water to thereby achieve cutting.

Similarly to the Steiner et al. patent, the Wolbarsht et al. patent requires water to be deposited onto the tooth before laser light is irradiated thereon. Specifically, the Wolbarsht et al. patent requires water to be inserted into pores of the material to be cut. Since many materials, such as tooth enamel, are not very porous, and since a high level of difficulty is associated with inserting water into the "pores" of many materials, this cutting method is somewhat less than optimal. Even the Steiner et al. patent has met with limited success, since the precision and accuracy of the cut is highly dependent upon the precision and accuracy of the water film on the material to be cut. In many cases, a controllable water film cannot be consistently maintained on the surface to be cut. For example, when the targeted tissue to be cut resides on the upper pallet, a controllable water film cannot be maintained.

The above-mentioned prior art systems have all sought in vain to obtain "cleanness" of cutting. In several dental applications, for example, a need to excise small amounts of soft tissues and/or hard tissues with a great degree of precision has existed. These soft tissues may include gingiva, frenum, and lesions and, additionally, the hard tissues may include dentin, enamel, bone, and cartilage. The term "cleanness" of cutting refers to extremely fine, smooth incisions which provide ideal bonding surfaces for various biomaterials. Such biomaterials include cements, glass ionomers and other composites used in dentistry or other sciences to fill holes in structures such as teeth or bone where tooth decay or some other defect has been removed. Even when an extremely fine incision has been achieved, the incision is often covered with a rough surface instead of the desired smooth surface required for ideal bonding.

One specific dental application, for example, which requires smooth and accurate cutting through both hard and soft tissues is implantology. According to the dental specialty of implantology, a dental implant can be installed in a person's mouth when that person has lost his or her teeth. The conventional implant installation technique is to cut through the soft tissue above the bone where the tooth is missing, and then to drill a hole into the bone. The hole in the bone is then threaded with a low-speed motorized tap, and a titanium implant is then screwed into the person's jaw. A synthetic tooth, for example, can be easily attached to the portion of the implant residing above the gum surface. One problem associated with the conventional technique occurs when the clinician drills into the patient's jaw to prepare the site for the implant. This drilling procedure generates a great deal of heat, corresponding to friction from the drilling instrument. If the bone is heated too much, it will die. Additionally, since the drilling instrument is not very precise, severe trauma to the jaw occurs after the drilling operation. The drilling operation creates large mechanical internal stress on the bone structure.

SUMMARY OF THE INVENTION

The present invention discloses an electromagnetically induced cutting mechanism, which can provide accurate cutting operations on hard and soft tissues, and other materials, as well. The electromagnetically induced cutter is capable of providing extremely fine and smooth incisions, irrespective of the cutting surface. Additionally, a user programmable combination of atomized particles allows for user control of various cutting parameters. The various cutting parameters may also be controlled by changing spray nozzles and electromagnetic energy source parameters. Applications for the present invention include medical, dental, industrial (etching, engraving, cutting and cleaning) and any other environments where an objective is to precisely remove surface materials without inducing thermal damage, uncontrolled cutting parameters, and/or rough surfaces inappropriate for ideal bonding. The present invention further does not require any films of water or any particularly porous surfaces to obtain very accurate and controllable cutting.

Drills, saws and osteotomes are standard mechanical instruments used in a variety of dental and medical applications. The limitations associated with these instruments include: temperature induced necrosis (bone death), aerosolized solid-particle release, limited access, lack of precision in cutting depth and large mechanical stress created on the tissue structure. The electromagnetically induced mechanical cutter of the present invention is uniquely suited for these dental and medical applications, such as, for example, implantology. In an implantology procedure the electromagnetically induced mechanical cutter is capable of accurately and efficiently cutting through both oral soft tissues overlaying the bone and also through portions of the jawbone itself. The electromagnetically induced mechanical cutter of the present invention does not induce thermal damage and does not create high internal structural stress on the patient's jaw, for example. After the patient's jaw is prepared with the electromagnetically induced mechanical cutter, traditional methods can be employed for threading the hole in the patient's jaw and inserting the dental implant. Similar techniques can be used for preparing hard tissue structures for insertion of other types of medical implants, such as pins, screws, wires, etc.

The electromagnetically induced mechanical cutter of the present invention includes an electromagnetic energy source, which focuses electromagnetic energy into a volume of air adjacent to a target surface. The target surface may be a tooth, for example. A user input device specifies whether either a high resolution or a low resolution cut is needed, and further specifies whether a deep penetration cut or a shallow penetration cut is needed. An atomizer generates a combination of atomized fluid particles, according to information from the user input device. The atomizer places the combination of atomized fluid particles into the volume of air adjacent to the target surface. The electromagnetic energy, which is focused into the volume of air adjacent to the target surface, is selected to have a wavelength suitable for the fluid particles. In particular, the wavelength of the electromagnetic energy should be substantially absorbed by the atomized fluid particles in the volume of air adjacent to the target surface to thereby explode the atomized fluid particles. Explosion of the atomized fluid particles imparts mechanical cutting forces onto the target surface.

The user input device may incorporate only a single dial for controlling the cutting efficiency, or may include a number of dials for controlling the fluid particle size, fluid particle velocity, spray cone angle, average laser power, laser repetition rate, fiberoptic diameter, etc. According to one feature of the present invention, the atomizer generates relatively small fluid particles when the user input specifies a high resolution cut, and generates relatively large fluid particles when the user input specifies a low resolution cut. The atomizer generates a relatively low density distribution of fluid particles when the user input specifies a deep penetration cut, and generates a relatively high density distribution of fluid particles when the user input specifies a shallow penetration cut. A relatively small fluid particle may have a diameter less than the wavelength of the electromagnetic energy and, similarly, a relatively large fluid particle may have a diameter which is greater than the wavelength of the electromagnetic energy.

The electromagnetic energy source preferably is an erbium, chromium, yttrium, scandium, gallium garnet (Er, Cr:YSGG) solid state laser, which generates electromagnetic energy having a wavelength in a range of 2.70 to 2.80 microns. According to other embodiments of the present invention, the electromagnetic energy source may be an erbium, yttrium, scandium, gallium garnet (Er:YSGG) solid state laser, which generates electromagnetic energy having a wavelength in a range of 2.70 to 2.80 microns; an erbium, yttrium, aluminum garnet (Er:YAG) solid state laser, which generates electromagnetic energy having a wavelength of 2.94 microns; chromium, thulium, erbium, yttrium, aluminum garnet (CTE:YAG) solid state laser, which generates electromagnetic energy having a wavelength of 2.69 microns; erbium, yttrium orthoaluminate (Er:YALO3) solid state laser, which generates electromagnetic energy having a wavelength in a range of 2.71 to 2.86 microns; holmium, yttrium, aluminum garnet (Ho:YAG) solid state laser, which generates electromagnetic energy having a wavelength of 2.10 microns; quadrupled neodymium, yttrium, aluminum garnet (quadrupled Nd:YAG) solid state laser, which generates electromagnetic energy having a wavelength of 266 nanometers; argon fluoride (ArF) excimer laser, which generates electromagnetic energy having a wavelength of 193 nanometers; xenon chloride (XeCl) excimer laser, which generates electromagnetic energy having a wavelength of 308 nanometers; krypton fluoride (KrF) excimer laser, which generates electromagnetic energy having a wavelength of 248 nanometers; and carbon dioxide (CO2), which generates electromagnetic energy having a wavelength in a range of 9 to 10.6 microns.

When the electromagnetic energy source is configured according to the preferred embodiment, the repetition rate is greater than 1 Hz, the pulse duration range is between 1 picosecond and 1000 microseconds, and the energy is greater than 1 milliJoule per pulse. According to one preferred operating mode of the present invention, the electromagnetic energy source has a wavelength of approximately 2.78 microns, a repetition rate of 20 Hz, a pulse duration of 140 microseconds, and an energy between 1 and 300 milliJoules per pulse. The atomized fluid particles provide the mechanical cutting forces when they absorb the electromagnetic energy within the interaction zone. These atomized fluid particles, however, provide a second function of cleaning and cooling the fiberoptic guide from which the electromagnetic energy is output.

The optical cutter of the present invention combats the problem of poor coupling between the two laser fiberoptics of FIG. 1. The optical cutter of the present invention provides a focusing optic for efficiently directing the energy from the first fiberoptic guide to the second fiberoptic guide, to thereby reduce dissipation of laser energy between the first fiberoptic guide and the second fiberoptic guide. This optical cutter includes a housing having a lower portion, an upper portion, and an interfacing portion. The first fiberoptic tube is surrounded at its upper portion by a first abutting member, and the second fiberoptic tube is surrounded at its proximal end by a second abutting member. A cap is placed over the second fiberoptic tube and the second abutting member. Either fiberoptic tube may be formed of calcium fluoride (CaF), calcium oxide (CaO2), zirconium oxide (ZrO2), zirconium fluoride (ZrF), sapphire, hollow waveguide, liquid core, TeX glass, quartz silica, germanium sulfide, arsenic sulfide, and germanium oxide (GeO2).

The electromagnetically induced mechanical cutter of the present invention efficiently and accurately cuts both hard and soft tissue. This hard tissue may include tooth enamel, tooth dentin, tooth cementum, bone, and cartilage, and the soft tissues may include skin, mucosa, gingiva, muscle, heart, liver, kidney, brain, eye, and vessels.

The invention, together with additional features and advantages thereof may best be understood by reference to the following description taken in connection with the accompanying illustrative drawings.

BRIEF DESCRIPTION OF THE DRAWINGS

FIG. 1 is a conventional optical cutter apparatus;

FIG. 2 is an optical cutter with the focusing optic of the present invention;

DESCRIPTION OF THE PRESENTLY PREFERRED EMBODIMENTS

Figure 3:
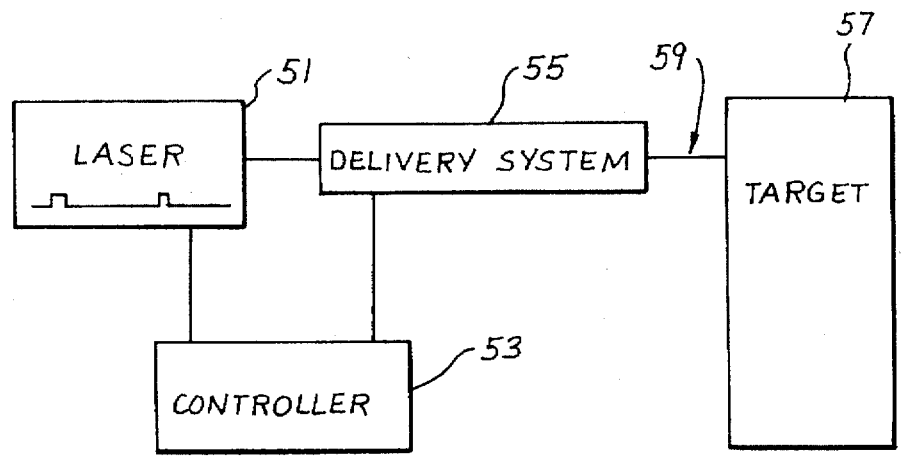
FIG. 3 is a schematic block diagram illustrating the electromagnetically induced mechanical cutter of the present invention.

FIG. 2 shows an optical cutter according to the present invention. The optical cutter 13 comprises many of the conventional elements shown in FIG. 1. A focusing optic 35 is placed between the two metal cylindrical objects 19 and 21. The focusing optic 35 prevents undesired dissipation of laser energy from the fiber guide tube 5. Specifically, energy from the fiber guide tube 5 dissipates slightly before being focused by the focusing optic 35. The focusing optic 35 focuses energy from the fiber guide tube 5 into the fiber guide tube 23. The efficient transfer of laser energy from the fiber guide tube 5 to the fiber guide tube 23 vitiates any need for the conventional air knife cooling system 11 (FIG. 1), since little laser energy is dissipated. The first fiber guide tube 5 comprises a trunk fiberoptic, which comprises one of calcium fluoride (CaF), calcium oxide (CaO2), zirconium oxide (ZrO2), zirconium fluoride (ZrF), sapphire, hollow waveguide, liquid core, TeX glass, quartz silica, germanium sulfide, arsenic sulfide, and germanium oxide (GeO2).

FIG. 3 is a block diagram illustrating the electromagnetically induced mechanical cutter of the present invention. An electromagnetic energy source 51 is coupled to both a controller 53 and a delivery system 55. The delivery system 55 imparts mechanical forces onto the target surface 57. As presently embodied, the delivery system 55 comprises a fiberoptic guide for routing the laser 51 into an interaction zone 59, located above the target surface 57. The delivery system 55 further comprises an atomizer for delivering user-specified combinations of atomized fluid particles into the interaction zone 59. The controller 53 controls various operating parameters of the laser 51, and further controls specific characteristics of the user-specified combination of atomized fluid particles output from the delivery system 55.

Figure 4:
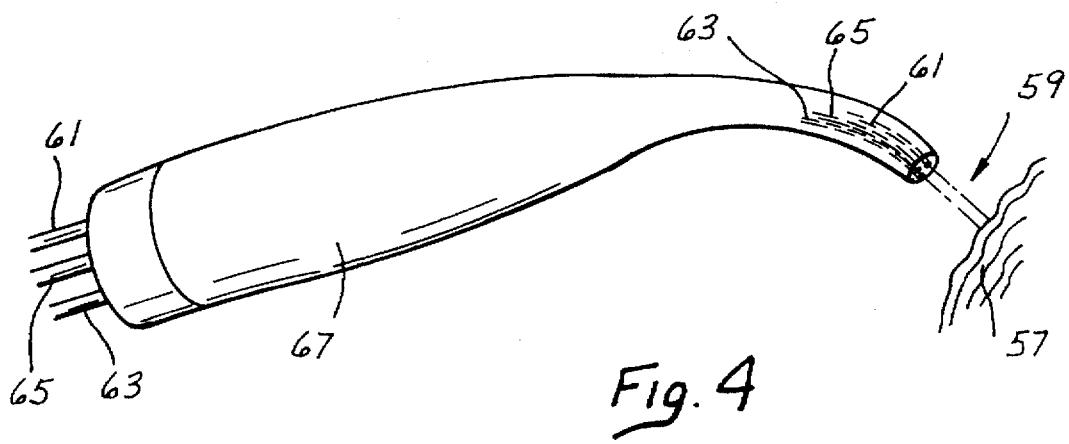
FIG. 4 illustrates one embodiment of the electromagnetically induced mechanical cutter of the present invention.

FIG. 4 shows a simple embodiment of the electromagnetically induced mechanical cutter of the present invention, in which a fiberoptic guide 61, an air tube 63, and a water tube 65 are placed within a hand-held housing 67. The water tube 65 is preferably operated under a relatively low pressure, and the air tube 63 is preferably operated under a relatively high pressure. The laser energy from the fiberoptic guide 61 focuses onto a combination of air and water, from the air tube 63 and the water tube 65, at the interaction zone 59. Atomized fluid particles in the air and water mixture absorb energy from the laser energy of the fiberoptic tube 61, and explode. The explosive forces from these atomized fluid particles impart mechanical cutting forces onto the target 57.

Turning back to FIG. 1, the prior art optical cutter focuses laser energy on a target surface at an area A, for example, and the electromagnetically induced mechanical cutter of the present invention focuses laser energy into an interaction zone B, for example. The prior art optical cutter uses the laser energy directly to cut tissue, and the electromagnetically induced mechanical cutter of the present invention uses the laser energy to expand atomized fluid particles to thus impart mechanical cutting forces onto the target surface. The prior art optic cutter must use a large amount of laser energy to cut the area of interest, and also must use a large amount of water to both cool this area of interest and remove cut tissue.

In contrast, the electromagnetically induced mechanical cutter of the present invention uses a relatively small amount of water and, further, uses only a small amount of laser energy to expand atomized fluid particles generated from the water. According to the electromagnetically induced mechanical cutter of the present invention, water is not needed to cool the area of surgery, since the exploded atomized fluid particles are cooled by exothermic reactions before they contact the target surface. Thus, atomized fluid particles of the present invention are heated, expanded, and cooled before contacting the target surface. The electromagnetically induced mechanical cutter of the present invention is thus capable of cutting without charring or discoloration.

Figure 5:
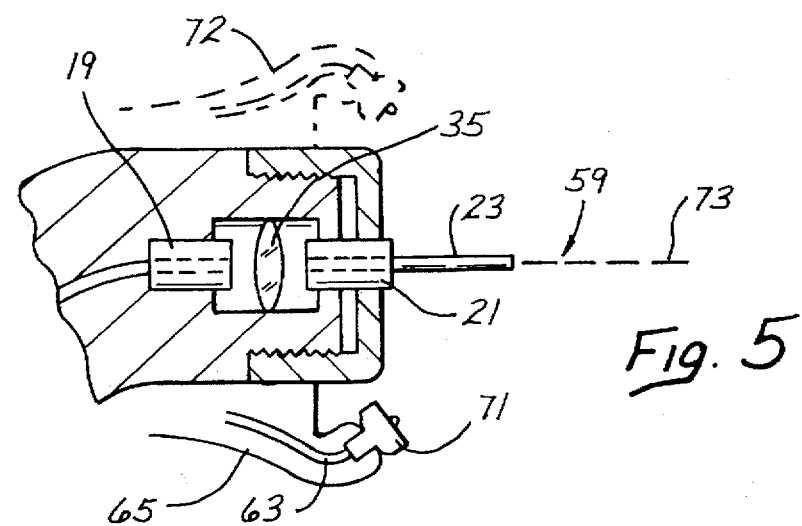
FIG. 5 illustrates the present preferred embodiment of the electromagnetically induced mechanical cutter of the present invention.

FIG. 5 illustrates the presently preferred embodiment of the electromagnetically induced mechanical cutter. The atomizer for generating atomized fluid particles comprises a nozzle 71, which may be interchanged with other nozzles (not shown) for obtaining various spatial distributions of the atomized fluid particles, according to the type of cut desired. A second nozzle 72, shown in phantom lines, may also be used. The cutting power of the electromagnetically induced mechanical cutter is further controlled by the user control 75. In a simple embodiment, the user control 75 controls the air and water pressure entering into the nozzle 71. The nozzle 71 is thus capable of generating many different user-specified combinations of atomized fluid particles and aerosolized sprays.

Intense energy is emitted from the fiberoptic guide 23. This intense energy is preferably generated from a coherent source, such as a laser. In the presently preferred embodiment, the laser comprises an erbium, chromium, yttrium, scandium, gallium garnet (Er, Cr:YSGG) solid state laser, which generates light having a wavelength in a range of 2.70 to 2.80 microns. As presently preferred, this laser has a wavelength of approximately 2.78 microns. Although the fluid emitted from the nozzle 71 preferably comprises water, other fluids may be used and appropriate wavelengths of the electromagnetic energy source may be selected to allow for high absorption by the fluid. Other possible laser systems include an erbium, yttrium, scandium, gallium garnet (Er:YSGG) solid state laser, which generates electromagnetic energy having a wavelength in a range of 2.70 to 2.80 microns; an erbium, yttrium, aluminum garnet (Er:YAG) solid state laser, which generates electromagnetic energy having a wavelength of 2.94 microns; chromium, thulium, erbium, yttrium, aluminum garnet (CTE:YAG) solid state laser, which generates electromagnetic energy having a wavelength of 2.69 microns; erbium, yttrium orthoaluminate (Er:YALO3) solid state laser, which generates electromagnetic energy having a wavelength in a range of 2.71 to 2.86 microns; holmium, yttrium, aluminum garnet (Ho:YAG) solid state laser, which generates electromagnetic energy having a wavelength of 2.10 microns; quadrupled neodymium, yttrium, aluminum garnet (quadrupled Nd:YAG) solid state laser, which generates electromagnetic energy having a wavelength of 266 nanometers; argon fluoride (ArF) excimer laser, which generates electromagnetic energy having a wavelength of 193 nanometers; xenon chloride (XeCl) excimer laser, which generates electromagnetic energy having a wavelength of 308 nanometers; krypton fluoride (KrF) excimer laser, which generates electromagnetic energy having a wavelength of 248 nanometers; and carbon dioxide (CO2), which generates electromagnetic energy having a wavelength in a range of 9.0 to 10.6 microns. Water is chosen as the preferred fluid because of its biocompatibility, abundance, and low cost. The actual fluid used may vary as long as it is properly matched (meaning it is highly absorbed) to the selected electromagnetic energy source (i.e. laser) wavelength.

The delivery system 55 for delivering the electromagnetic energy includes a fiberoptic energy guide or equivalent which attaches to the laser system and travels to the desired work site. Fiberoptics or waveguides are typically long, thin and lightweight, and are easily manipulated. Fiberoptics can be made of calcium fluoride (CaF), calcium oxide (CaO2), zirconium oxide (ZrO2), zirconium fluoride (ZrF), sapphire, hollow waveguide, liquid core, TeX glass, quartz silica, germanium sulfide, arsenic sulfide, germanium oxide (GeO2), and other materials. Other delivery systems include devices comprising mirrors, lenses and other optical components where the energy travels through a cavity, is directed by various mirrors, and is focused onto the targeted cutting site with specific lenses. The preferred embodiment of light delivery for medical applications of the present invention is through a fiberoptic conductor, because of its light weight, lower cost, and ability to be packaged inside of a handpiece of familiar size and weight to the surgeon, dentist, or clinician. In industrial applications, non-fiberoptic systems may be used.

The nozzle 71 is employed to create an engineered combination of small particles of the chosen fluid. The nozzle 71 may comprise several different designs including liquid only, air blast, air assist, swirl, solid cone, etc. When fluid exits the nozzle 71 at a given pressure and rate, it is transformed into particles of user-controllable sizes, velocities, and spatial distributions.

Figure 6:
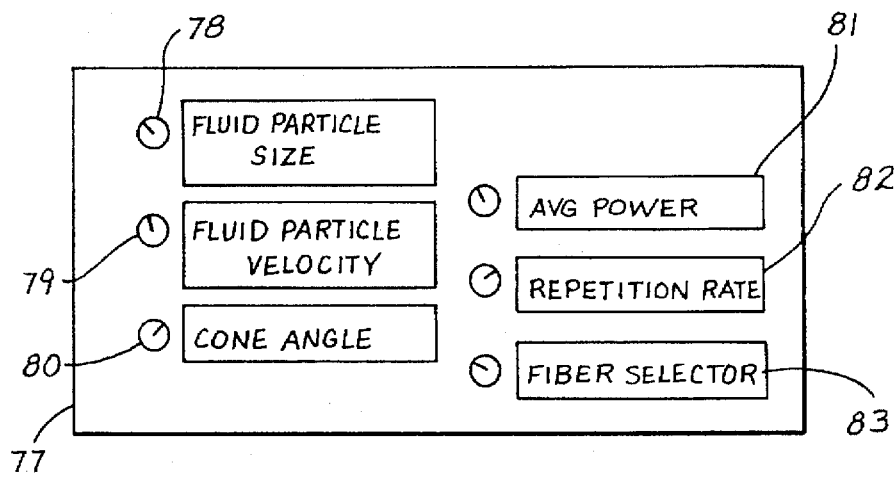
FIG. 6 illustrates a control panel for programming the combination of atomized fluid particles according to the presently preferred embodiment.

FIG. 6 illustrates a control panel 77 for allowing user-programmability of the atomized fluid particles. By changing the pressure and flow rates of the fluid, for example, the user can control the atomized fluid particle characteristics. These characteristics determine absorption efficiency of the laser energy, and the subsequent cutting effectiveness of the electromagnetically induced mechanical cutter. This control panel may comprise, for example, a fluid particle size control 78, a fluid particle velocity control 79, a cone angle control 80, an average power control 81, a repetition rate 82, and a fiber selector 83.

The cone angle may be controlled, for example, by changing the physical structure of the nozzle 71. For example, various nozzles 71 may be interchangeably placed on the electromagnetically induced mechanical cutter. Alternatively, the physical structure of a single nozzle 71 may be changed.

Figure 7:
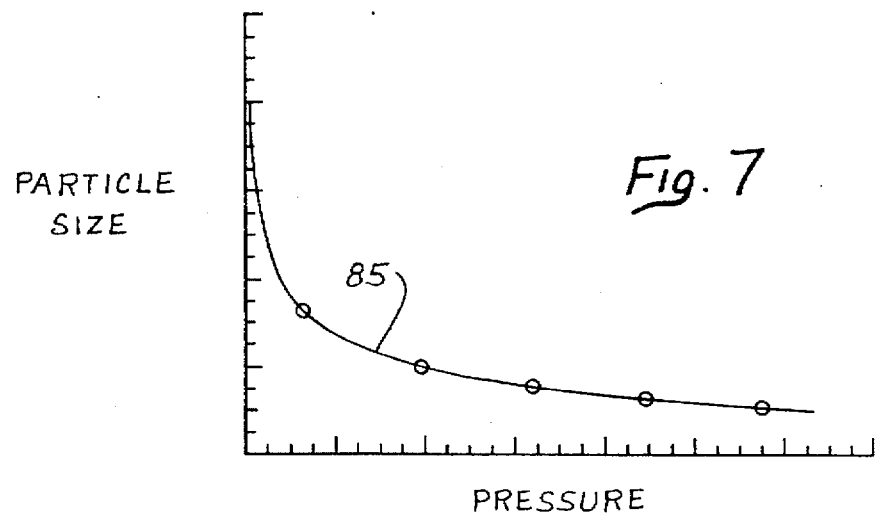
FIG. 7 is a plot of particle size versus fluid pressure.
Figure 8:
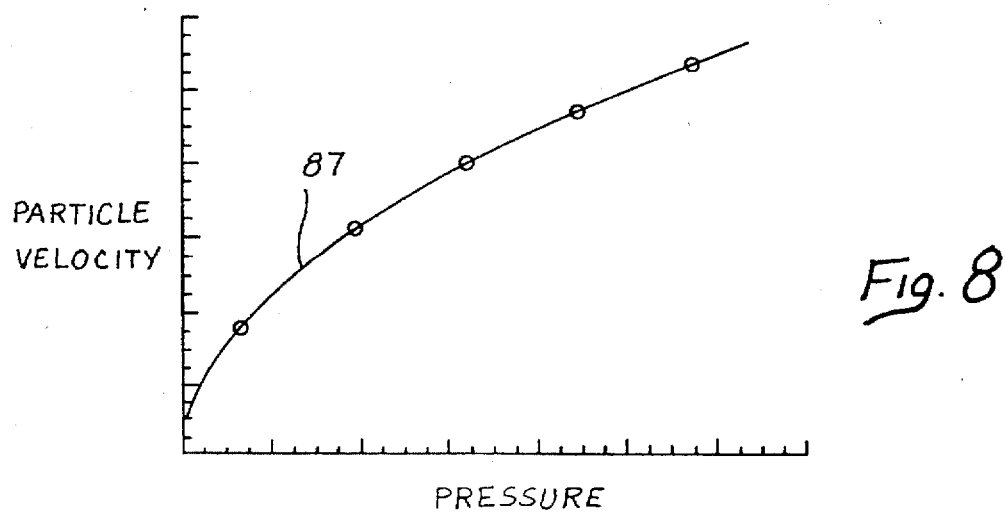
FIG. 8 is a plot of particle velocity versus fluid pressure.

FIG. 7 illustrates a plot 85 of mean fluid particle size versus pressure. According to this figure, when the pressure through the nozzle 71 is increased, the mean fluid particle size of the atomized fluid particles decreases. The plot 87 of FIG. 8 shows that the mean fluid particle velocity of these atomized fluid particles increases with increasing pressure.

According to the present invention, materials are removed from a target surface by mechanical cutting forces, instead of by conventional thermal cutting forces. Laser energy is used only to induce mechanical forces onto the targeted material. Thus, the atomized fluid particles act as the medium for transforming the electromagnetic energy of the laser into the mechanical energy required to achieve the mechanical cutting effect of the present invention. The laser energy itself is not directly absorbed by the targeted material. The mechanical interaction of the present invention is safer, faster, and eliminates the negative thermal side-effects typically associated with conventional laser cutting systems.

The fiberoptic guide 23 (FIG. 5) can be placed into close proximity of the target surface. This fiberoptic guide 23, however, does not actually contact the target surface. Since the atomized fluid particles from the nozzle 71 are placed into the interaction zone 59, the purpose of the fiberoptic guide 23 is for placing laser energy into this interaction zone, as well. A novel feature of the present invention is the formation of the fiberoptic guide 23 of sapphire. Regardless of the composition of the fiberoptic guide 23, however, another novel feature of the present invention is the cleaning effect of the air and water, from the nozzle 71, on the fiberoptic guide 23.

Applicants have found that this cleaning effect is optimal when the nozzle 71 is pointed somewhat directly at the target surface. For example, debris from the mechanical cutting are removed by the spray from the nozzle 71.

Additionally, applicants have found that this orientation of the nozzle 71, pointed toward the target surface, enhances the cutting efficiency of the present invention. Each atomized fluid particle contains a small amount of initial kinetic energy in the direction of the target surface. When electromagnetic energy from the fiberoptic guide 23 contacts an atomized fluid particle, the spherical exterior surface of the fluid particle acts as a focusing lens to focus the energy into the water particle's interior.

Figure 9:
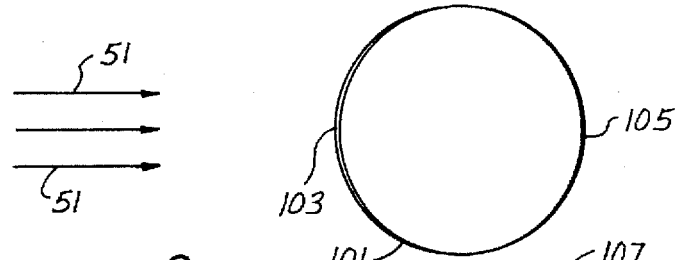
FIG. 9 is a schematic diagram illustrating a fluid particle, a source of electromagnetic energy, and a target surface according to the present invention.
Figure 9:
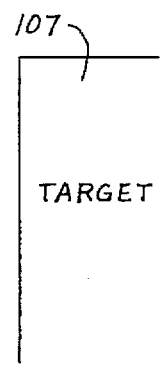

As shown in FIG. 9, the water particle 101 has an illuminated side 103, a shaded side 105, and a particle velocity 107. The focused electromagnetic energy is absorbed by the water particle 101, causing the interior of the water particle to heat and explode rapidly. This exothermic explosion cools the remaining portions of the exploded water particle 101. The surrounding atomized fluid particles further enhance cooling of the portions of the exploded water particle 101. A pressure-wave is generated from this explosion. This pressure-wave, and the portions of the exploded water particle 101 of increased kinetic energy, are directed toward the target surface 107. The incident portions from the original exploded water particle 101, which are now traveling at high velocities with high kinetic energies, and the pressure-wave, impart strong, concentrated, mechanical forces onto the target surface 107.

These mechanical forces cause the target surface 107 to break apart from the material surface through a "chipping away" action. The target surface 107 does not undergo vaporization, disintegration, or charring. The chipping away process can be repeated by the present invention until the desired amount of material has been removed from the target surface 107. Unlike prior art systems, the present invention does not require a thin layer of fluid. In fact, it is preferred that a thin layer of fluid does not cover the target surface, since this insulation layer would interfere with the above-described interaction process.

Figure 10:
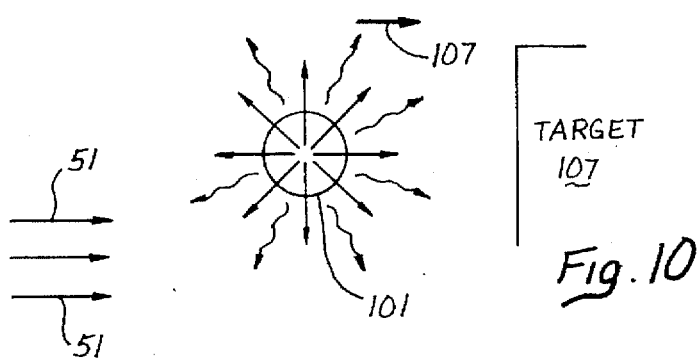
FIG. 10 is a schematic diagram illustrating the "grenade" effect of the present invention.
Figure 10:
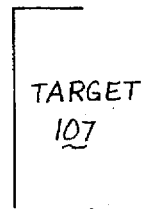
Figure 11:
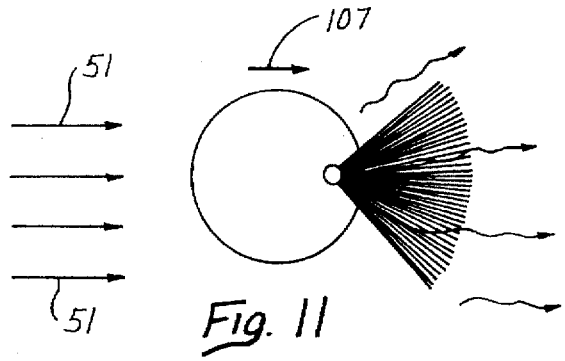
FIG. 11 is a schematic diagram illustrating the "explosive ejection" effect of the present invention.
Figure 11:
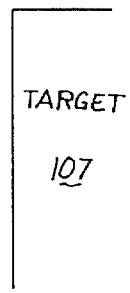
Figure 12:
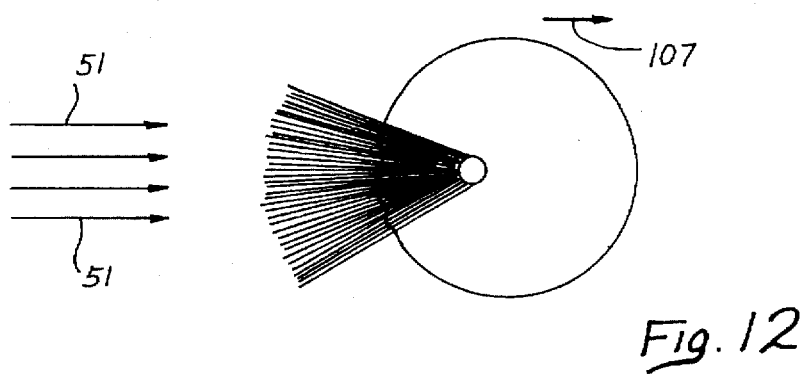
FIG. 12 is a schematic diagram illustrating the "explosive propulsion" effect of the present invention.
Figure 12:
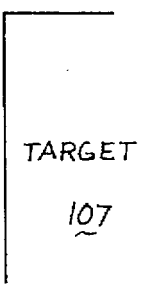

FIGS. 10, 11 and 12 illustrate various types of absorptions of the electromagnetic energy by atomized fluid particles. The nozzle 71 is preferably configured to produce atomized sprays with a range of fluid particle sizes narrowly distributed about a mean value. The user input device for controlling cutting efficiency may comprise a simple pressure and flow rate gauge 75 (FIG. 5) or may comprise a control panel as shown in FIG. 6, for example. Upon a user input for a high resolution cut, relatively small fluid particles are generated by the nozzle 71. Relatively large fluid particles are generated for a user input specifying a low resolution cut. A user input specifying a deep penetration cut causes the nozzle 71 to generate a relatively low density distribution of fluid particles, and a user input specifying a shallow penetration cut causes the nozzle 71 to generate a relatively high density distribution of fluid particles. If the user input device comprises the simple pressure and flow rate gauge 75 of FIG. 5, then a relatively low density distribution of relatively small fluid particles can be generated in response to a user input specifying a high cutting efficiency. Similarly, a relatively high density distribution of relatively large fluid particles can be generated in response to a user input specifying a low cutting efficiency. Other variations are also possible.

These various parameters can be adjusted according to the type of cut and the type of tissue. Hard tissues include tooth enamel, tooth dentin, tooth cementum, bone, and cartilage. Soft tissues, which the electromagnetically induced mechanical cutter of the present invention is also adapted to cut, include skin, mucosa, gingiva, muscle, heart, liver, kidney, brain, eye, and vessels. Other materials may include glass and semiconductor chip surfaces, for example. A user may also adjust the combination of atomized fluid particles exiting the nozzle 71 to efficiently implement cooling and cleaning of the fiberoptics 23 (FIG. 5), as well. According to the presently preferred embodiment, the combination of atomized fluid particles may comprise a distribution, velocity, and mean diameter to effectively cool the fiberoptic guide 23, while simultaneously keeping the fiberoptic guide 23 clean of particular debris which may be introduced thereon by the surgical site.

Looking again at FIG. 9, electromagnetic energy contacts each atomized fluid particle 101 on its illuminated side 103 and penetrates the atomized fluid particle to a certain depth. The focused electromagnetic energy is absorbed by the fluid, inducing explosive vaporization of the atomized fluid particle 101.

The diameters of the atomized fluid particles can be less than, almost equal to, or greater than the wavelength of the incident electromagnetic energy. In each of these three cases, a different interaction occurs between the electromagnetic energy and the atomized fluid particle. FIG. 10 illustrates a case where the atomized fluid particle diameter is less than the wavelength of the electromagnetic energy ($d<\lambda$). This case causes the complete volume of fluid inside of the fluid particle 101 to absorb the laser energy, inducing explosive vaporization. The fluid particle 101 explodes, ejecting its contents radially. Applicants refer to this phenomena as the "explosive grenade" effect. As a result of this interaction, radial pressure-waves from the explosion are created and projected in the direction of propagation. The direction of propagation is toward the target surface 107, and in the presently preferred embodiment, both the laser energy and the atomized fluid particles are traveling substantially in the direction of propagation.

The resulting portions from the explosion of the water particle 101, and the pressure-wave, produce the "chipping away" effect of cutting and removing of materials from the target surface 107. Thus, according to the "explosive grenade" effect shown in FIG. 10, the small diameter of the fluid particle 101 allows the laser energy to penetrate and to be absorbed violently within the entire volume of the liquid. Explosion of the fluid particle 101 can be analogized to an exploding grenade, which radially ejects energy and shrapnel. The water content of the fluid particle 101 is evaporated due to the strong absorption within a small volume of liquid, and the pressure-waves created during this process produce the material cutting process.

FIG. 11 shows a case where the fluid particle 101 has a diameter, which is approximately equal to the wavelength of the electromagnetic energy ($d \approx \lambda$). According to this "explosive ejection" effect, the laser energy travels through the fluid particle 101 before becoming absorbed by the fluid therein. Once absorbed, the fluid particle's shaded side heats up, and explosive vaporization occurs. In this case, internal particle fluid is violently ejected through the fluid particle's shaded side, and moves rapidly with the explosive pressure-wave toward the target surface. As shown in FIG. 11, the laser energy is able to penetrate the fluid particle 101 and to be absorbed within a depth close to the size of the particle's diameter. The center of explosive vaporization in the case shown in FIG. 11 is closer to the shaded side 105 of the moving fluid particle 101. According to this "explosive ejection" effect shown in FIG. 11, the vaporized fluid is violently ejected through the particle's shaded side toward the target surface 107.

A third case shown in FIG. 12 is the "explosive propulsion" effect. In this case, the diameter of the fluid particle is larger than the wavelength of the electromagnetic energy ($d>\lambda$). In this case, the laser energy penetrates the fluid particle 101 only a small distance through the illuminated surface 103 and causes this illuminated surface 103 to vaporize. The vaporization of the illuminated surface 103 tends to propel the remaining portion of the fluid particle 101 toward the targeted material surface 107. Thus, a portion of the mass of the initial fluid particle 101 is converted into kinetic energy, to thereby propel the remaining portion of the fluid particle 101 toward the target surface with a high kinetic energy. This high kinetic energy is additive to the initial kinetic energy of the fluid particle 101. The effects shown in FIG. 12 can be visualized as a micro-hydro rocket with a jet tail, which helps propel the particle with high velocity toward the target surface 107. The exploding vapor on the illuminated side 103 thus supplements the particle's initial forward velocity.

Figure 13:
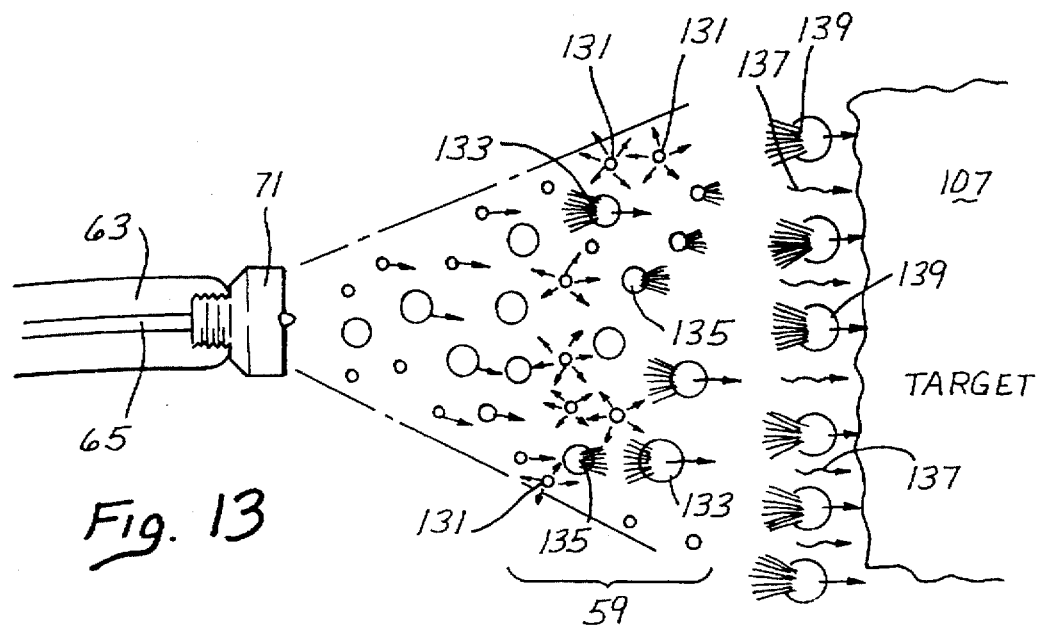
FIG. 13 is a schematic diagram illustrating a combination of FIGS. 10–12.

The combination of FIGS. 10-12 is shown in FIG. 13. The nozzle 71 produces the combination of atomized fluid particles which are transported into the interaction zone 59. The laser 51 is focused on this interaction zone 59. Relatively small fluid particles 131 explode via the "grenade" effect, and relatively large fluid particles 133 explode via the "explosive propulsion" effect. Medium sized fluid particles, having diameters approximately equal to the wavelength of the laser 51 and shown by the reference number 135, explode via the "explosive ejection" effect. The resulting pressure-waves 137 and exploded fluid particles 139 impinge upon the target surface 107.

Figure 14:
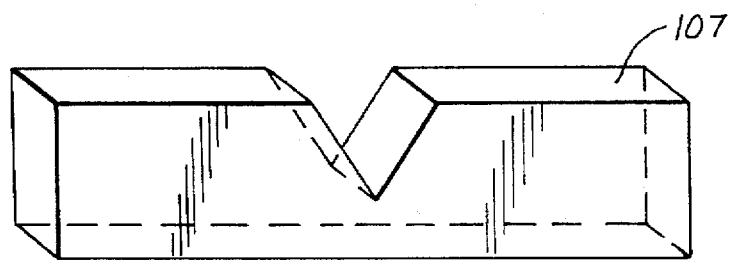
FIG. 14 is a schematic diagram illustrating the "cleanness" of cut obtained by the present invention.
Figure 15:
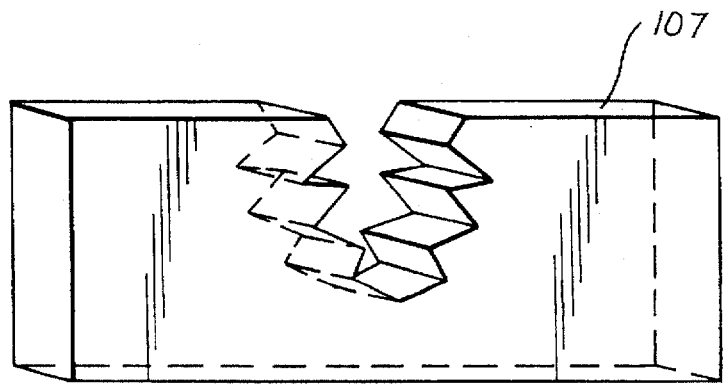
FIG. 15 is a schematic diagram illustrating the roughness of cut obtained by prior art systems.

FIG. 14 illustrates the clean, high resolution cut produced by the electromagnetically induced mechanical cutter of the present invention. Unlike the cut of the prior art shown in FIG. 15, the cut of the present invention is clean and precise. Among other advantages, this cut provides an ideal bonding surface, is accurate, and does not stress remaining materials surrounding the cut.

Although an exemplary embodiment of the invention has been shown and described, many changes, modifications and substitutions may be made by one having ordinary skill in the art without necessarily departing from the spirit and scope of this invention.

What is claimed is:

1. An apparatus for imparting mechanical forces onto a target surface, comprising:

an atomizer for placing atomized fluid particles into an inneraction zone, the interaction zone being defined as a volume above the target surface;

an electromagnetic energy source for focusing electromagnetic energy into the interaction zone, the electromagnetic energy having a wavelength which is substantially absorbed by the atomized fluid particles in the interaction zone, the absorption of the electromagetic energy by the atomized fluid particles causing the atomized fluid particles to impart disruptive mechanical forced onto the target surface;

a user control for accepting a user input, which specifies a cutting efficiency of the apparatus; and wherein at least one physical characteristic of the atomized fluid particles is controlled by the user input.

2. The apparatus for imparting mechanical forces onto a target surface according to claim 1, wherein the electromagnetic energy source is an erbium, chromium, yttrium scandium gallium garnet (Er, Cr:YSGG) solid state laser, which generates electromagnetic energy having a wavelength of approximately 2.78 microns.

3. The apparatus for imparting mechanical forces onto a target surface according to claim 1, wherein the fluid comprises water, and wherein the electromagnetic energy source consists of at least one of the following:
   (a) erbium, yttrium, scandium, gallium garnet (Er:YSGG) solid state laser, which generates electromagnetic energy having a wavelength in a range of 2.70 to 2.80 microns;
   (b) erbium, yttrium, aluminum garnet (Er:YAG) solid state laser, which generates electromagnetic energy having a wavelength of 2.94 microns;
   (c) chromium, thulium, erbium, yttrium, aluminum garnet (CTE:YAG) solid state laser, which generates electromagnetic energy having a wavelength of 2.69 microns;
   (d) erbium, yttrium orthoaluminate (Er:YALO3) solid state laser, which generates electromagnetic energy having a wavelength in a range of 2.71 to 2.86 microns;
   (e) holmium, yttrium, aluminum garnet (Ho:YAG) solid state laser, which generates electromagnetic energy having a wavelength of 2.10 microns;
   (f) quadrupled neodymium, yttrium, aluminum garnet (quadrupled Nd:YAG) solid state laser, which generates electromagnetic energy having a wavelength of 266 nanometers;
   (g) argon fluoride (ArF) excimer laser, which generates electromagnetic energy having a wavelength of 193 nanometers;
   (h) xenon chloride (XeCl) excimer laser, which generates electromagnetic energy having a wavelength of 308 nanometers;
   (i) krypton fluoride (KrF) excimer laser, which generates electromagnetic energy having a wavelength of 248 nanometers; and
   (j) carbon dioxide (CO2), which generates electromagnetic energy having a wavelength in a range of 9.0 to 10.6 microns.

4. The apparatus for imparting mechanical forces onto a target surface according to claim 1, wherein the energy is delivered through a fiberoptic, and wherein the atomized fluid particles contact the fiberoptic to thereby cool and clean the fiberoptic.

5. The apparatus for imparting mechanical forces onto a target surface according to claim 4, wherein the atomized fluid particles contact the fiberoptic to thereby remove particulate debris from the fiberoptic.

6. The apparatus for imparting mechanical forces onto a target surface according to claim 4, wherein the fiberoptic comprises sapphire.

7. The apparatus for imparting mechanical forces onto a target surface according to claim 1, wherein the fluid particles comprise water, and wherein the electromagnetic energy source is an erbium, chromium, yttrium, scandium, gallium garnet (Er, Cr:YSGG) solid state laser, which generates electromagnetic energy having a wavelength in a range of 2.70 to 2.80 microns.

8. The apparatus for imparting mechanical forces onto a target surface according to claim 7, wherein the Er, Cr:YSGG solid state laser has a repetition rate greater than 1 Hz, a pulse duration range between 1 picosecond and 1000 microseconds, and an energy greater than 10 milliJoules per pulse.

9. An electromagnetically induced mechanical cutter for removing portions of a target surface, comprising:

a user control for inputting a user-specified combination of atomized fluid particles, the user-specified combination of atomized fluid particles corresponding to a user-specified average size, spatial distribution, and velocity of atomized fluid particles;

an atomizer responsive to the user control, for generating the user-specified combination of atomized fluid particles, and for placing the user-specified combination of atomized fluid particles into an interaction zone, the interaction zone being defined as a volume above the target surface; and an electromagnetic energy source for focusing electromagnetic energy into the interaction zone, the electromagnetic energy having a wavelength which is substantially absorbed by a portion of atomized fluid particles of the user-specified combination of atomized fluid particles in the interaction zone, the absorption of the electromagnetic energy by the portion of atomized fluid particles causing the portion of atomized fluid particles to impart distuptive mechanical forces onto the target surface.

10. The electromagnetically induced mechanical cutter for removing portions of a target surface according to claim 9, wherein the fluid consists of at least water, and wherein the electromagnetic energy source comprises one of the following:
(a) erbium, yttrium, scandium, gallium garnet (Er:YSGG) solid state laser, which generates electromagnetic energy having a wavelength in a range of 2.70 to 2.80 microns;
(b) erbium, yttrium, aluminum garnet (Er:YAG) solid state laser, which generates electromagnetic energy having a wavelength of 2.94 microns;
(c) chromium, thulium, erbium, yttrium, aluminum garnet (CTE:YAG) solid state laser, which generates electromagnetic energy having a wavelength of 2.69 microns;
(d) erbium, yttrium orthoaluminate (Er:YALO3) solid state laser, which generates electromagnetic energy having a wavelength in a range of 2.71 to 2.86 microns;
(e) holmium, yttrium, aluminum garnet (Ho:YAG) solid state laser, which generates electromagnetic energy having a wavelength of 2.10 microns;
(f) quadrupled neodymium, yttrium, aluminum garnet (quadrupled Nd:YAG) solid state laser, which generates electromagnetic energy having a wavelength of 266 nanometers;
(g) argon fluoride (ArF) excimer laser, which generates electromagnetic energy having a wavelength of 193 nanometers;
(h) xenon chloride (XeCl) excimer laser, which generates electromagnetic energy having a wavelength of 308 nanometers;
(i) krypton fluoride (KrF) excimer laser, which generates electromagnetic energy having a wavelength of 248 nanometers; and
(j) carbon dioxide (CO2), which generates electromagnetic energy having a wavelength in a range of 9.0 to 10.6 microns.

11. The electromagnetically induced mechanical cutter for removing portions of a target surface according to claim 9, wherein the fluid comprises water, and wherein the electromagnetic energy source is an erbium, chromium, yttrium, scandium, gallium garnet (Er, Cr:YSGG) solid state laser, which generates light having a wavelength in a range of 2.70 to 2.80 microns.

12. The electromagnetically induced mechanical cutter for removing portions of a target surface according to claim 11, wherein the Er, Cr:YSGG solid state laser has a repetition rate greater than 1 Hz, a pulse duration range between 1 picosecond and 1000 microseconds, and an energy greater than 1 milliJoule per pulse.

13. The electromagnetically induced mechanical cutter for removing portions of a target surface according to claim 11, wherein the Er, Cr:YSGG solid state laser has a repetition rate of 20 Hz, a pulse duration of 140 microseconds, and an energy between 1 and 300 milliJoules per pulse.

* * * * *

UNITED STATES PATENT AND TRADEMARK OFFICE
CERTIFICATE OF CORRECTION

PATENT NO. : 5,741,247
DATED : April 21, 1998
INVENTOR(S) : Ioana M. Rizoiu et al.

It is certified that error appears in the above-identified patent and that said Letters Patent is hereby corrected as shown below:

Column 11, line 27, Claim 1; delete "inneraction" and insert in place thereof --interaction--.

Column 11, line 37, Claim 1; delete "forced" and insert in place thereof --forces--.

Signed and Sealed this

Eighteenth Day of May, 1999

*Attest:*

Q. TODD DICKINSON

*Attesting Officer*      *Acting Commissioner of Patents and Trademarks*

UNITED STATES PATENT AND TRADEMARK OFFICE
CERTIFICATE OF CORRECTION

PATENT NO. : 5,741,247                                                    Page 1 of 1
DATED      : April 21, 1998
INVENTOR(S) : Rizoiu et al.

It is certified that error appears in the above-identified patent and that said Letters Patent is hereby corrected as shown below:

Drawings,
Sheet 3 of 5, should show Figure 5 to include Reference 75 as shown below:

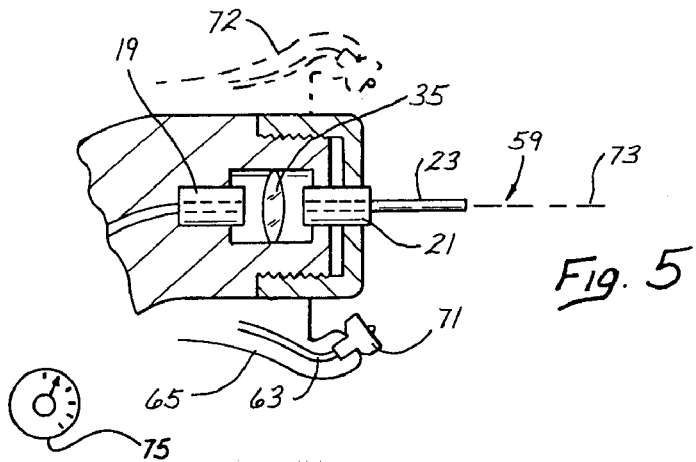

Signed and Sealed this

Twenty-eighth Day of June, 2005

JON W. DUDAS
*Director of the United States Patent and Trademark Office*